United States Patent
Yau et al.

(10) Patent No.: US 8,406,909 B2
(45) Date of Patent: Mar. 26, 2013

(54) METHOD OF DESIGNING DENTAL-IMPLANT PROSTHESIS

(75) Inventors: Hong-Tzong Yau, Chiayi County (TW); Chuan-Chu Kuo, Chiayi County (TW); Jiun-Ren Chen, Yunlin County (TW); Chien-An Chen, Kaohsiung County (TW); Lee-Sen Tsou, Hsinchu (TW)

(73) Assignee: Pou Yu Biotechnology Co., Ltd. (TW)

( * ) Notice: Subject to any disclaimer, the term of this patent is extended or adjusted under 35 U.S.C. 154(b) by 295 days.

(21) Appl. No.: 12/923,016

(22) Filed: Aug. 30, 2010

(65) Prior Publication Data
US 2011/0123954 A1    May 26, 2011

(30) Foreign Application Priority Data
Nov. 26, 2009 (TW) ................ 98140432 A

(51) Int. Cl.
*G06F 19/00* (2011.01)
(52) U.S. Cl. ............... 700/98; 433/24; 433/72; 433/173
(58) Field of Classification Search ............. 700/98; 433/24, 72, 173
See application file for complete search history.

(56) References Cited

U.S. PATENT DOCUMENTS

| | | | |
|---|---|---|---|
| 2003/0096210 A1* | 5/2003 | Rubbert et al. | 433/24 |
| 2004/0229185 A1* | 11/2004 | Knopp | 433/24 |
| 2006/0079981 A1* | 4/2006 | Rubbert et al. | 700/98 |
| 2006/0093988 A1* | 5/2006 | Swaelens et al. | 433/76 |
| 2006/0099547 A1* | 5/2006 | Knopp | 433/24 |
| 2008/0280247 A1* | 11/2008 | Sachdeva et al. | 433/24 |
| 2008/0280258 A1* | 11/2008 | Wen | 433/213 |
| 2009/0291407 A1* | 11/2009 | Kuo | 433/24 |
| 2009/0325125 A1* | 12/2009 | DiAngelo et al. | 433/173 |

\* cited by examiner

*Primary Examiner* — Mohammad Ali
*Assistant Examiner* — Anthony Whittington
(74) *Attorney, Agent, or Firm* — Bacon & Thomas, PLLC

(57) ABSTRACT

A method of designing a dental-implant prosthesis includes the steps of arranging a referential jig and combining the referential jig into a fixture installed in a patient's oral cavity, the referential jig having at least one feature point, the fixture having a connection interface, the referential jig having an opposite-joint interface; scanning the patient's oral cavity to acquire an oral digital data and a referential-jig digital data having at least one feature-point digital data; selecting one digital dental-implant prosthesis from a prosthetic database in a computer, a digital positioning jig overlapping the digital dental-implant prosthesis for combination with the connection interface, and proceeding with overlapping and localization of the digital positioning jig and the referential-jig digital data to combine the referential-jig digital data into the connection interface; and adjusting the position, size, and angle of the digital dental-implant prosthesis to acquire the digital dental-implant prosthesis which is most suitable to the patient.

10 Claims, 16 Drawing Sheets a) Arrange a referential jig in a patient's oral cavity b) Scanning c) Localization d) Adjustment and designing

METHOD OF DESIGNING DENTAL-IMPLANT PROSTHESIS

BACKGROUND OF THE INVENTION

1. Field of the Invention

The present invention relates generally to artificial dental implantation, and more particularly, to a method of designing a dental-implant prosthesis.

2. Description of the Related Art

A conventional dental-implant design initially needs to acquire a bite mold from a patient's oral cavity. The bite mold includes at least one analog planted in the patient's bone under simulation. Next, a dental-implant prosthesis, e.g. artificial abutment, is created for combination into the analog. Finally, a dental crown is created and mounted to the dental-implant prosthesis to complete the whole design of the dental implant.

Because the connection interface of the aforesaid analog is not obvious, scanning the aforesaid bite mold can only come up with digital data of the bite mold and fails to accurately acquire digital data of the analog. Besides, the combination of the analog and the abutment is provided with specific configuration and combinative directionality, such that the relevant design and adjustment can be applied to the abutment when the digital data of the analog cannot be accurately acquired. However, it is highly possible to come up with an inaccurate abutment to further affect the combinative relationship that the abutment is positioned in the analog, such that it is failed to design the optimal formation of the abutment. In this way, no definite information about the dental occlusion is available to possibly cause malocclusion of artificial tooth/teeth installed later, and no definite information about the dental arrangement to lessen the aesthetic appearance of the artificial tooth/teeth after the dental implantation.

SUMMARY OF THE INVENTION

The primary objective of the present invention is to provide a method of designing a dental-implant prosthesis, which does not need to acquire a solid bite mold from the patient's oral cavity.

The secondary objective of the present invention is to provide a method of designing a dental-implant prosthesis, which can accurately position the prosthesis to further come up with the most proper formation of the prosthesis after adjustment in such a way the definite information about the dental occlusion can be acquired to enable good occlusion of artificial tooth/teeth installed later.

The foregoing objectives of the present invention are attained by the method including the following steps of a) arranging a referential jig under the condition that there is a fixture in a patient's oral cavity, and then combining the referential jig into the fixture, the referential jig having at least one feature point exposed outside the fixture and dental gum of the patient's oral cavity, the fixture having a connection interface formed at a top side thereof, the referential jig having an opposite-joint interface formed at a bottom side thereof and corresponding to the connection interface; b) scanning the patient's oral cavity by a scanner to acquire an oral digital data, a referential jig digital data, and a feature-point digital data, and then saving those digital data into a computer; c) selecting one of digital dental-implant prostheses from a prosthetic database, a digital positioning jig overlapping the dental-implant prosthesis and having the same pattern and feature point as those of the referential jig, the digital positioning jig fitting the connection interface for combination with the connection interface, the digital dental-implant prosthesis having the same opposite-joint interface formed at a bottom side thereof as that of the referential jig; operating the computer to proceed with overlapping and localization by means of the feature points of the digital positioning jig and the feature-point digital data of the referential jig digital data; removing the referential-jig digital data and the digital positioning jig after the overlapping and localization are completed; inferring a digital fixture, a digital connection interface, and respective positions of the digital fixture and the digital connection interface via the digital dental-implant prosthesis to further acquire a configuration digital data of the combination and localization of the digital dental-implant prosthesis and the connection interface; and d) identifying whether the combination of the digital dental-implant prosthesis and the dental-implant digital data is accurate according to the configuration digital data and if it is not accurate, adjust the inaccuracy to accuracy. In addition, according to the space relationship between the oral digital data and the digital dental-implant prosthesis, the relationship among the digital dental-implant prosthesis, abutting tooth/teeth, and opposite tooth/teeth in the patient's oral cavity can be identified to further acquire the digital dental-implant prosthesis, which is the most applicable to the patient, by adjusting the position, size, and angle of the digital dental-implant prosthesis.

DETAILED DESCRIPTION OF PREFERRED EMBODIMENTS

Figure 1:
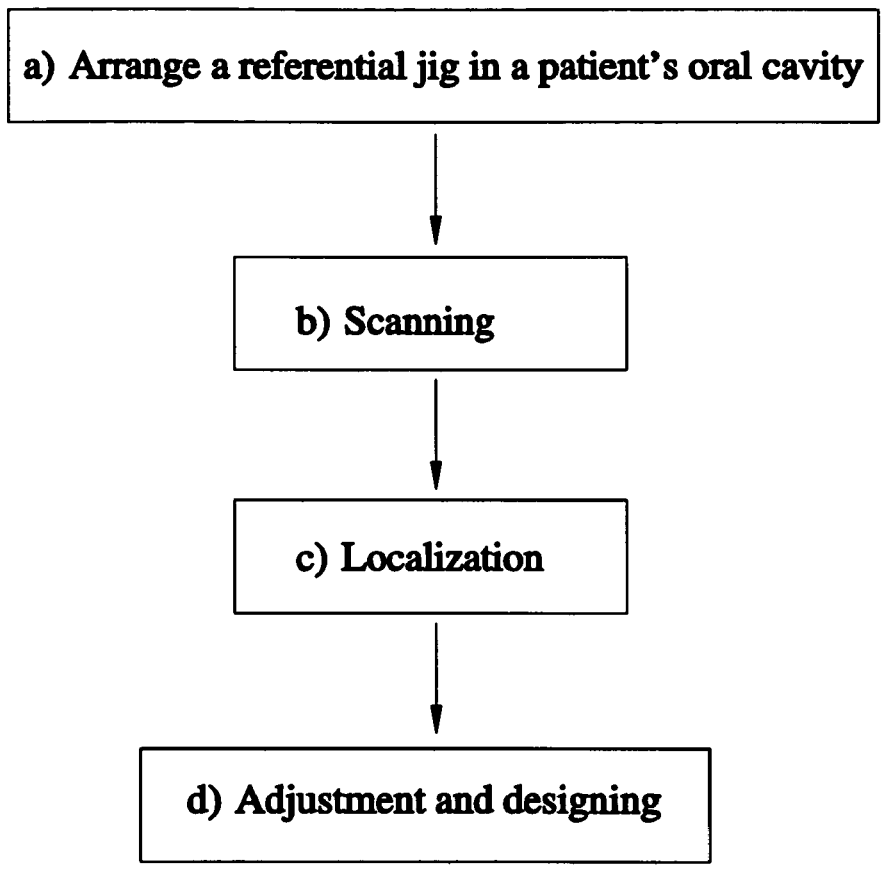
FIG. 1 is a flow chart of a first preferred embodiment of the present invention.
Figure 2:
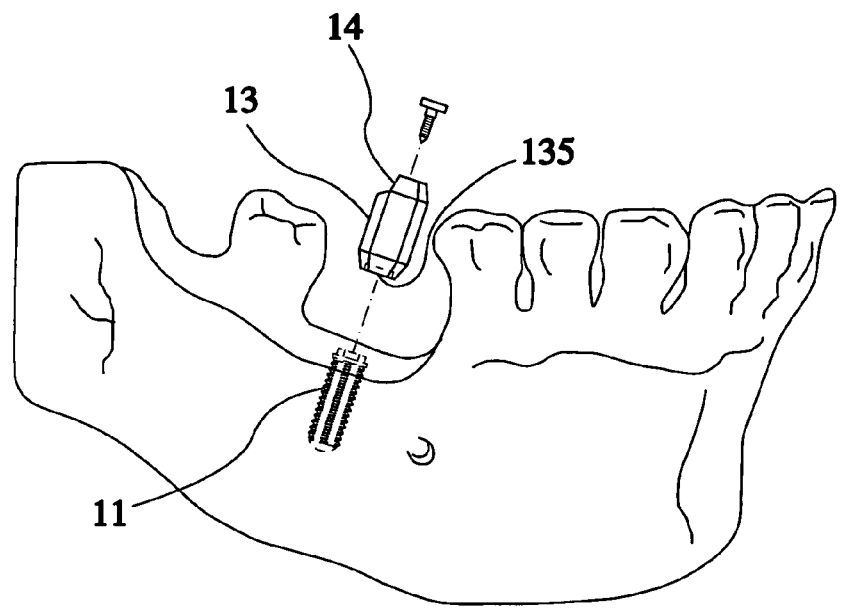
FIG. 2 is a schematic view of the first preferred embodiment of the present invention, showing that there is a fixture in an oral cavity.
Figure 3:
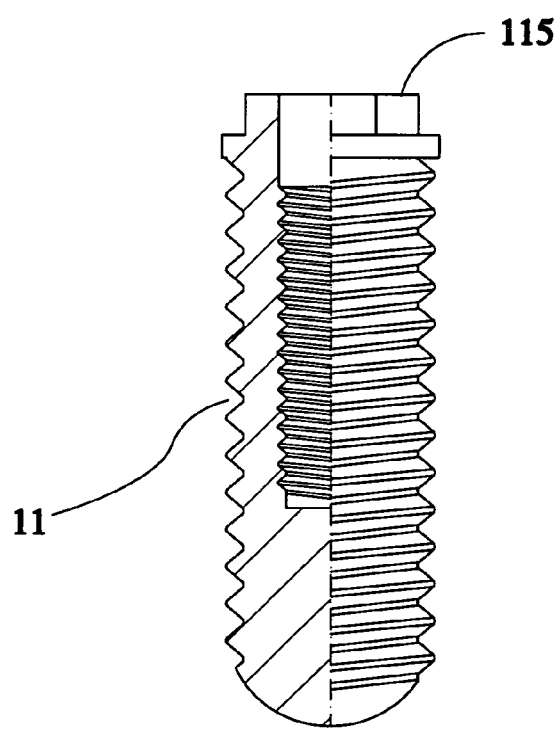
FIG. 3 is a sectional view of a part of the first preferred embodiment of the present invention, showing the structure of the fixture.
Figure 4:
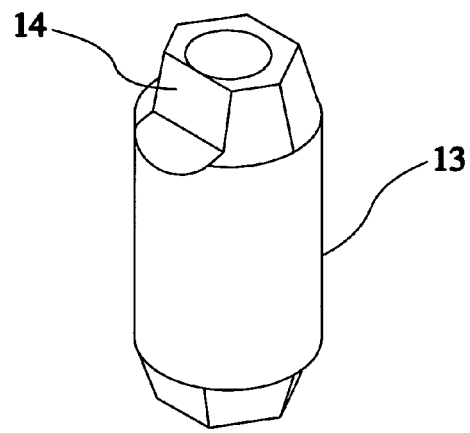
FIG. 4 is a perspective view of the first preferred embodiment of the present invention, showing the structure of a referential jig.
Figure 5:
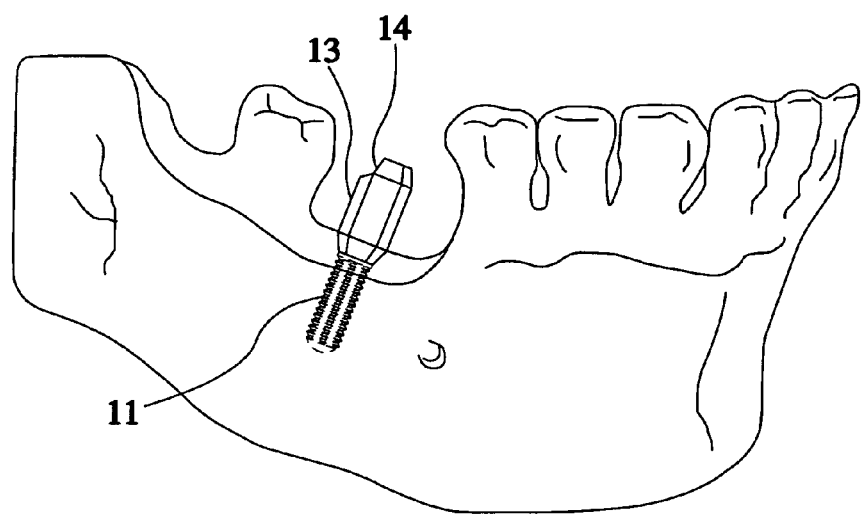
FIG. 5 is similar to FIG. 2, showing that the referential jig is installed to the fixture.
Figure 6:
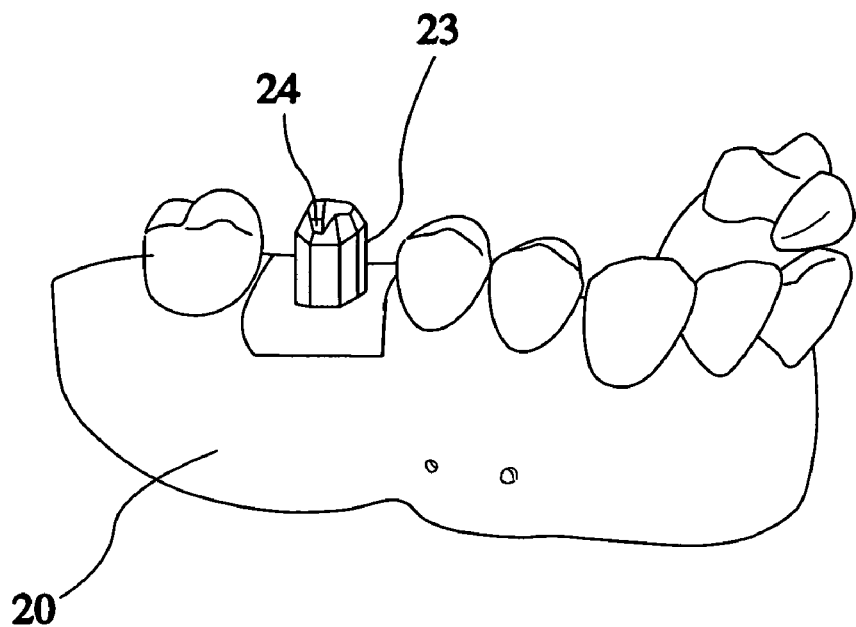
FIG. 6 is another schematic view of the first preferred embodiment of the present invention, showing the pattern of each digital data acquired by scanning.
Figure 7:
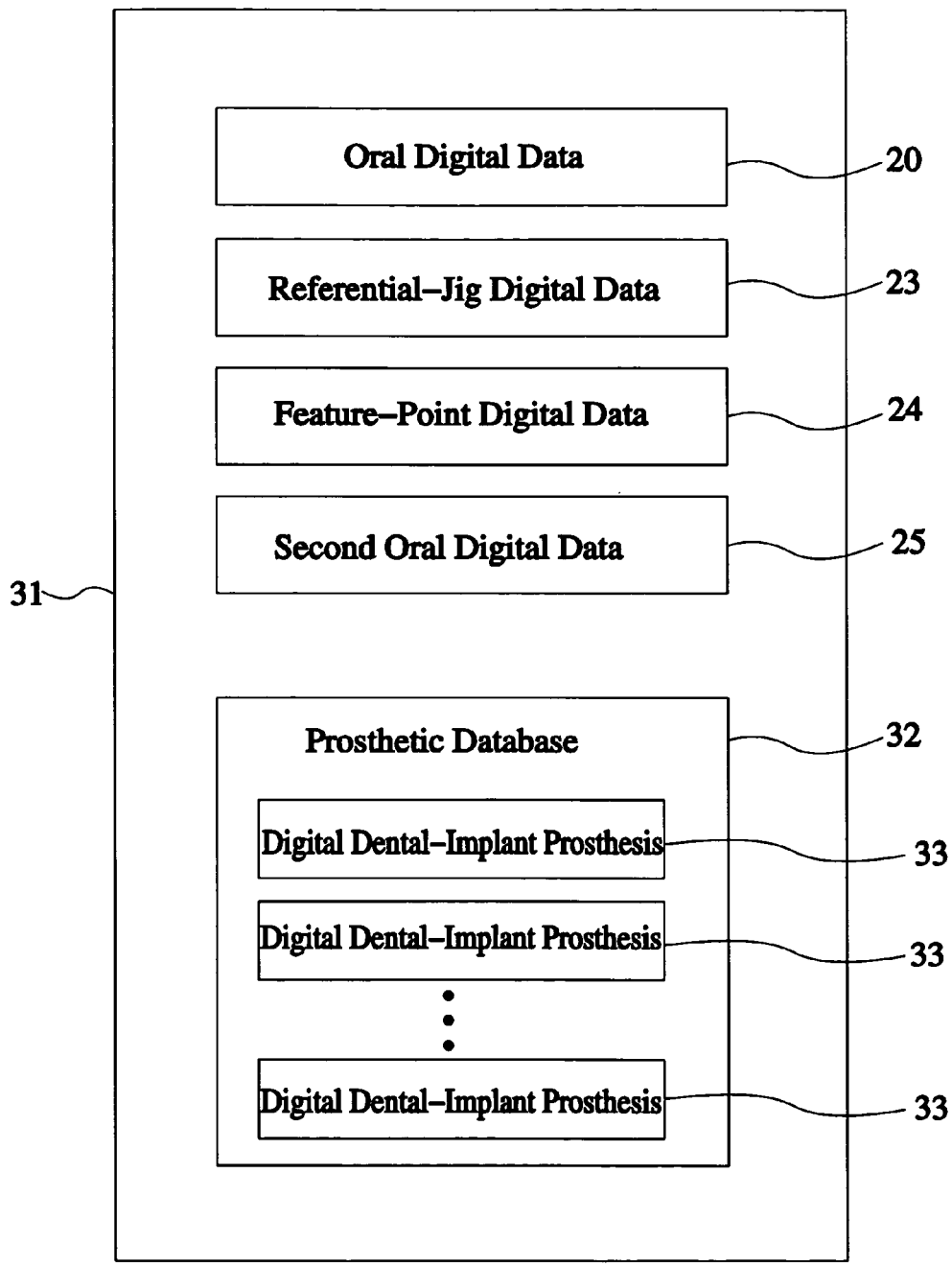
FIG. 7 is a block diagram of the first preferred embodiment of the present invention, showing the data saved in a computer.
Figure 8:
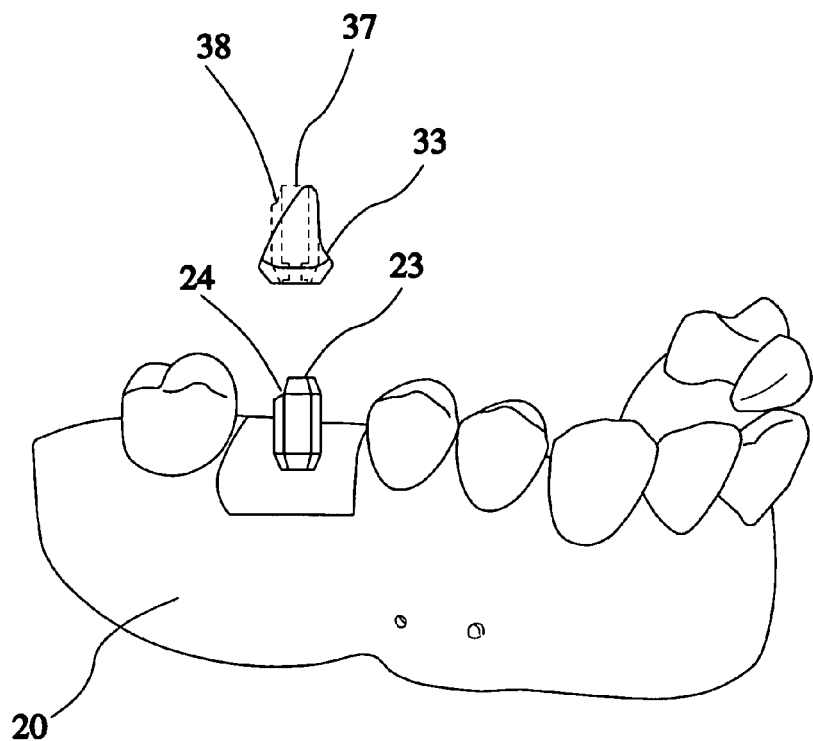
FIG. 8 is similar to FIG. 6, showing that a digital dental-implant prosthesis has not positioned to a referential jig digital data.
Figure 9:
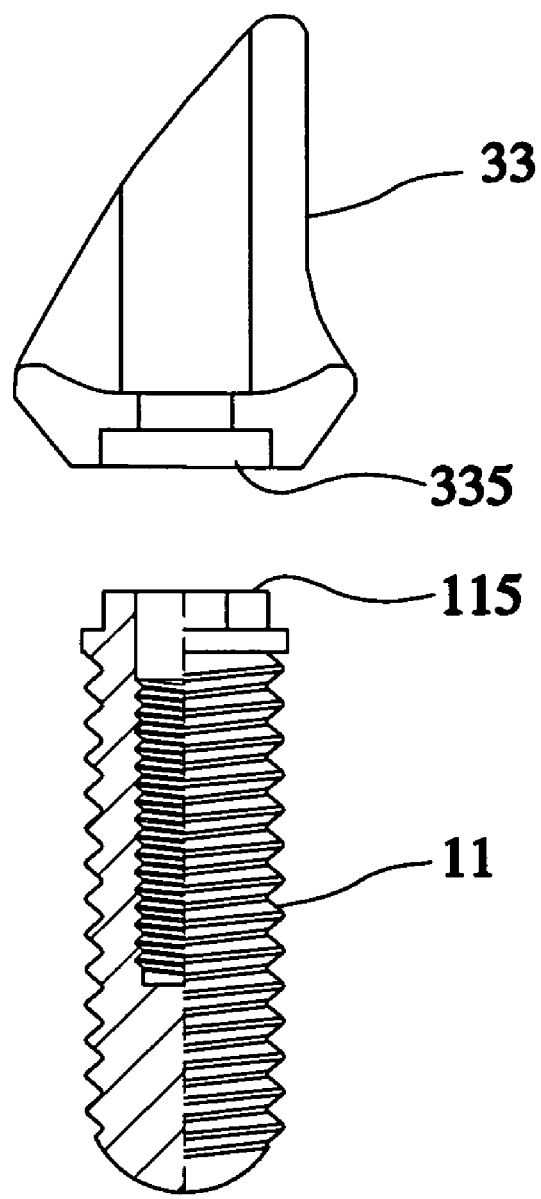
FIG. 9 is a schematic view of a part of the first preferred embodiment of the present invention, showing that the digital dental-implant prosthesis is separated from a inferred fixture.
Figure 10:
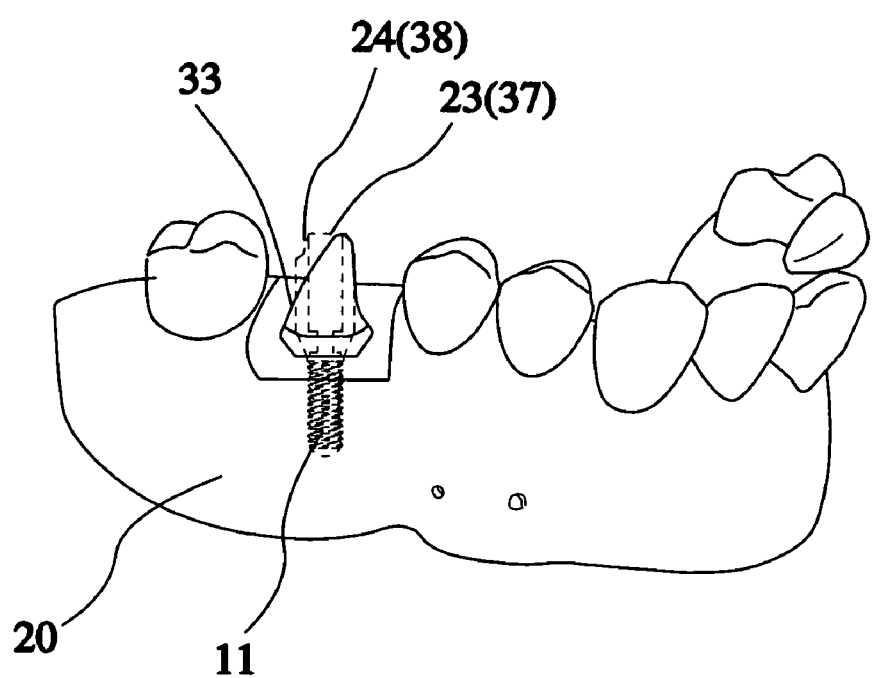
FIG. 10 is similar to FIG. 8, showing that the digital dental-implant prosthesis is positioned to the referential jig digital data.
Figure 11:
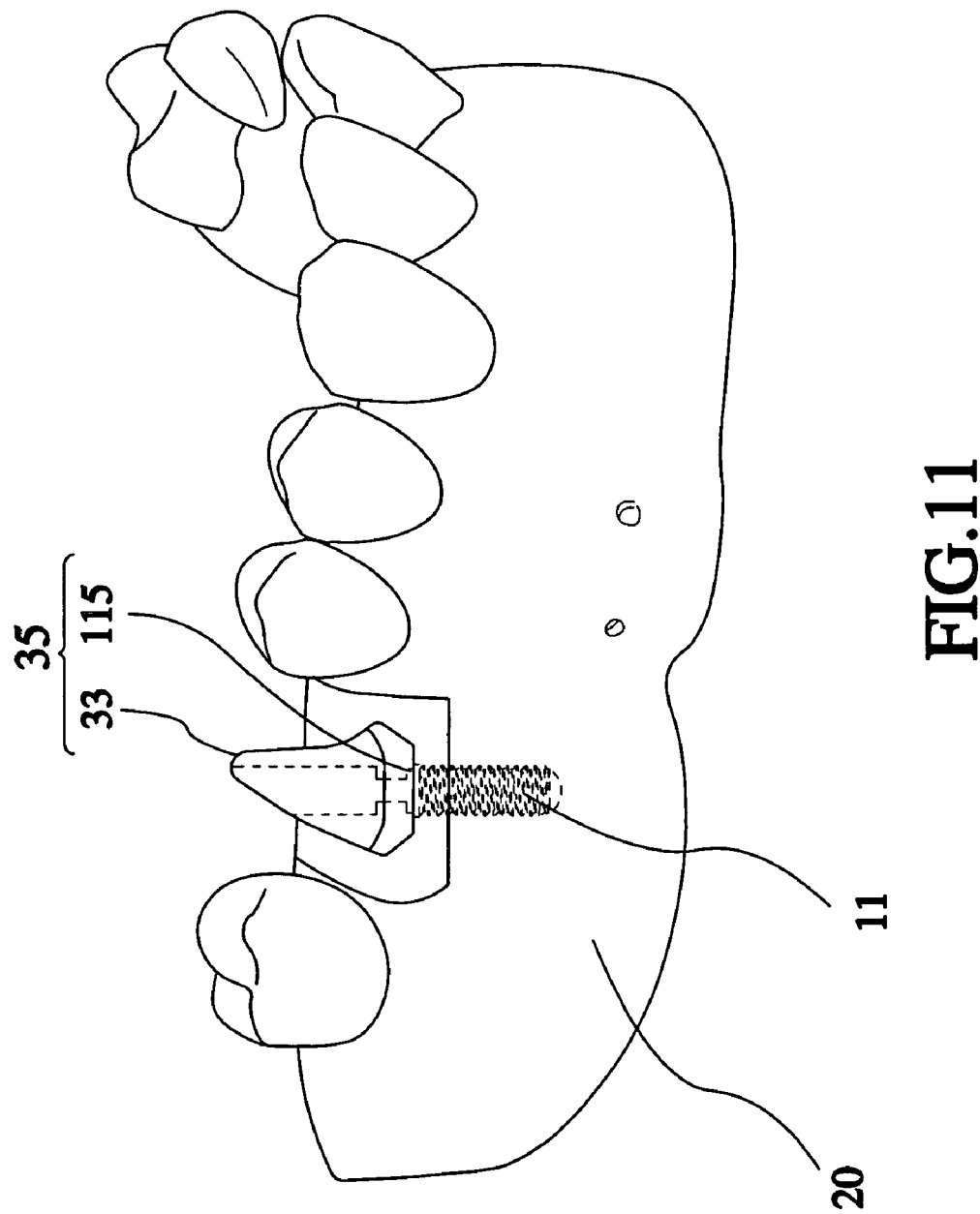
FIG. 11 is a schematic view of the first preferred embodiment of the present invention, showing that the referential jig digital data and the digital positioning jig are removed.
Figure 12:
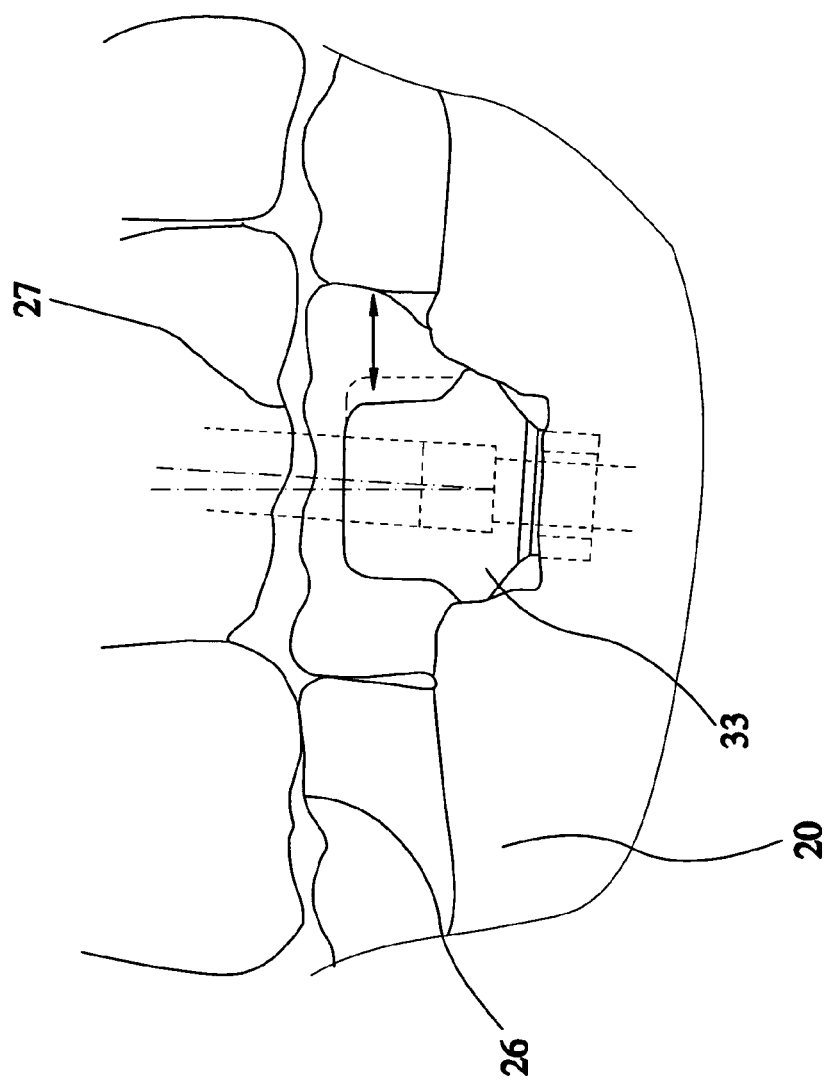
FIG. 12 is another schematic view of the first preferred embodiment of the present invention, showing that the relationship between the digital dental-implant prosthesis and the adjacent teeth and opposite tooth in the oral cavity.
Figure 13:
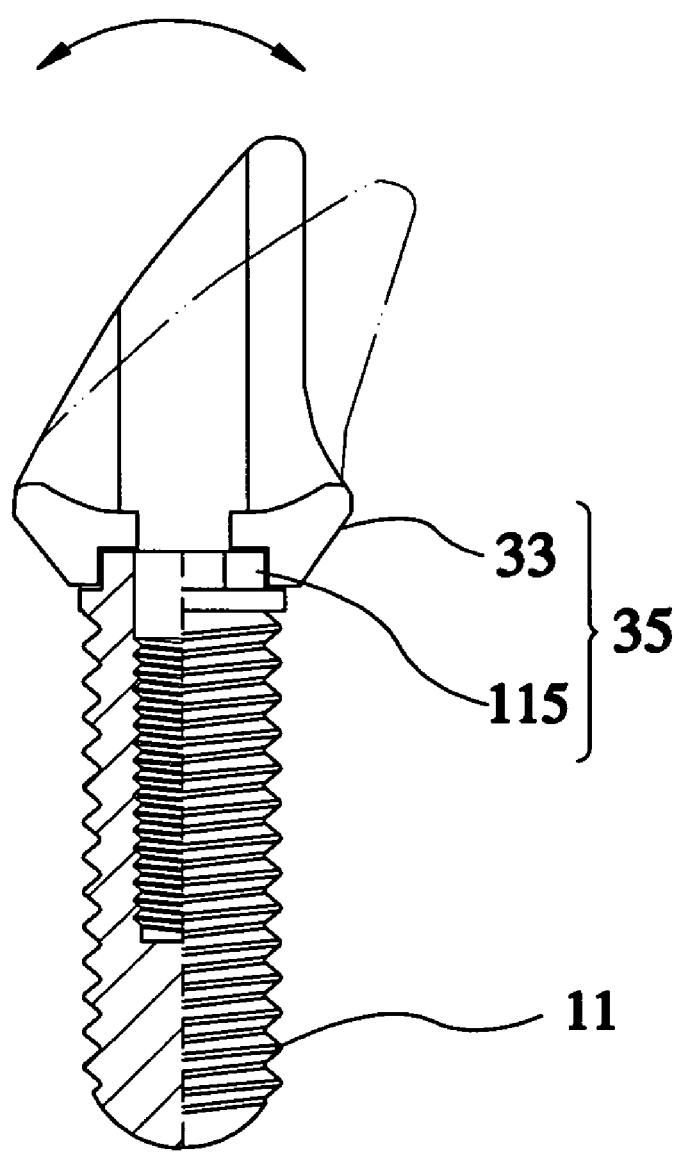
FIG. 13 is similar to FIG. 9, showing that the digital dental-implant prosthesis is being adjusted.
Figure 14:
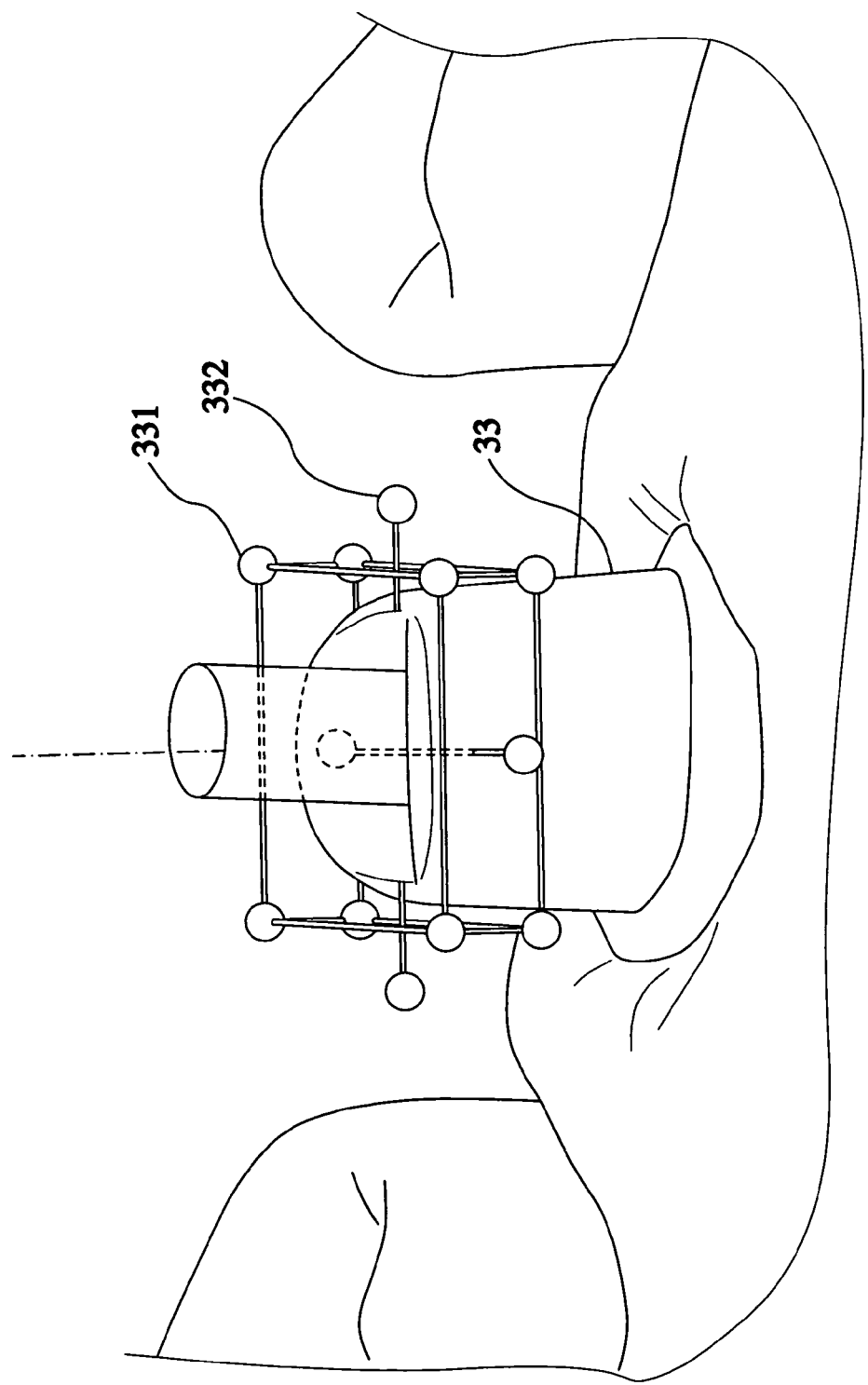
FIG. 14 is another schematic view of the first preferred embodiment of the present invention, showing that the computer is used to operate zoom-adjustment points and size-adjustment points.
Figure 15:
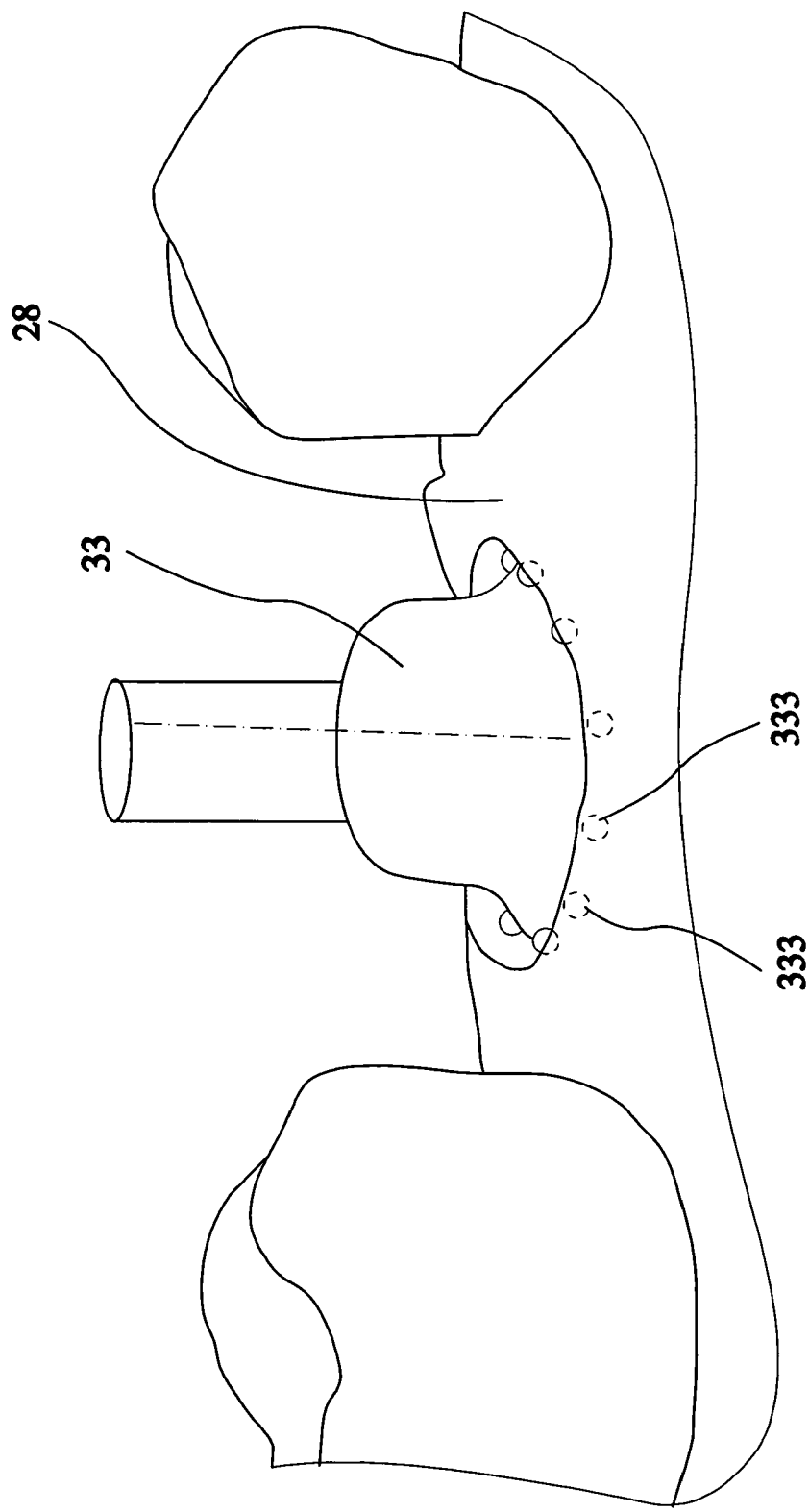
FIG. 15 is similar to FIG. 13, showing that the computer is used to operate position-adjustment points.

Referring to FIG. 1, a method of designing a dental-implant prosthesis in accordance with a first preferred embodiment of the present invention includes the following steps.

a) As shown in FIGS. 2-5, under the condition that there is a fixture 11 in a patient's oral cavity, arrange a referential jig 13 corresponding to the fixture 11, and then combine the selected referential jig 13 into the fixture 11. The referential jig 13 includes a plurality of feature points 14 exposed outside the fixture 11 and dental gum in the patient's oral cavity. The fixture 11 includes a connection interface 115 formed at a top side thereof. The referential jig 13 includes an opposite-joint interface 135 formed at a bottom side thereof and corresponding to the connection interface 115. In this way, the referential jig 13 can be combined into the fixture 11 when the connection interface 115 is connected with the opposite-joint interface 135. The feature points 14 are convex or concave or both. In this embodiment, the feature points 14 are concave.

b) Scan the patient's oral cavity by a scanner (not shown) to acquire an oral digital data 20, a referential-jig digital data 23, and a feature-point digital data 24, as shown in FIG. 6 showing the digital pattern not the solid one. After the patient's oral cavity is scanned, remove the referential jig 13 from the fixture 11 and then scan the patient's oral cavity by the scanner again to acquire a second oral digital data 25. The second oral digital data 25 includes digital data of the dental gum around the fixture 11. Next, save those digital data into a computer 31 as shown in FIG. 7.

c) Referring to FIGS. 7-9, select one of digital dental-implant prostheses 33 from a prosthetic database 32 in the computer 31. The selected digital dental-implant prosthesis 33 is a digital abutment in this embodiment and overlaps a digital positioning jig 37. The digital positioning jig 37 has the same pattern and feature points 38 as those of the referential jig 13 and can be connected with the connection interface 115. The selected digital dental-implant prosthesis 33 includes an opposite-joint interface 335 formed at a bottom side thereof as the same as the opposite-joint interface 135 of the referential jig 13 for connection with the connection interface 115. Referring to FIG. 10, operate the computer 31 to proceed with overlapping and localization by means of the feature points 38 and the feature-point digital data 24 of the referential jig digital data 23. In this way, if the relationship of localization of the corresponding feature point 34 and the feature-point digital data 24 is accurate, it can be inferred that the combination of the dental-implant prosthesis 33, the fixture 11, and the connection interface 115 is accurate; if the localization is inaccurate, it can be adjusted to be accurate. In FIG. 10, the fixture 11 is inferred based on the aforesaid combinative relationship. Referring to FIG. 11, remove the referential jig digital data 23 and the digital positioning jog 37, after the overlapping and localization are completed. Next, infer a digital fixture, a digital connection interface, and respective positions of the digital fixture and the digital connection interface according to the digital dental-implant prosthesis 33 to further acquire a configuration digital data 35 of the combination and localization of the digital dental-implant prosthesis 33 and the connection interface 115. The configuration digital data 35 includes angles and axial directions of the digital dental-implant prosthesis 33 and the digital fixture. What FIGS. 8-11 show is digital not solid, such that the fixtures 11 in those drawings are inferred to be shown in dotted line.

d) Referring to FIG. 12, identify the relationship among the digital dental-implant prosthesis 33, abutting teeth 26, and an opposite tooth 27 according to the space relationship between the oral digital data 20 and the digital dental-implant prosthesis 33. Next, referring to FIGS. 13-15, adjust the position, size, and angle of the digital dental-implant prosthesis 33 as well as its relationship with a dental gum 28 to acquire the digital dental-implant prosthesis 33 which is the most applicable to the patient. During the actual adjustment, as shown in FIG. 14, the digital dental-implant prosthesis 33 includes a plurality of zoom-adjustment points 331, angle-adjustment points 332, and position-adjustment points 333. A user can operate the mouse cursor in the computer 31 to click on and drag the zoom-adjustment points 331 to further adjust the size of the digital dental-implant prosthesis 33. The user can also operate the mouse cursor in the computer 31 to click on and drag the angle-adjustment points 332 to further adjust the angle of the digital dental-implant prosthesis 33. As shown in FIG. 15, while it is intended to adjust the positional relationship between the digital dental-implant prosthesis 33 and the dental gum 28, the user can operate the computer 31 to click on and drag the position-adjustment points 333. In light of the above steps, the digital dental-implant prosthesis 33 which is the most suitable to the patient can be schemed out. When the actual production is intended, it only needs to compute the digital data of the digital dental-implant prosthesis 33 by means of a processing software of the computer 31 and then to produce a solid dental-implant prosthesis by a machine tool. What FIGS. 12-15 show is digital not solid.

In addition, the user can also design a corresponding dental crown (not shown) according to the digital dental-implant prosthesis 33 to complete the whole dental implant.

Figure 16:
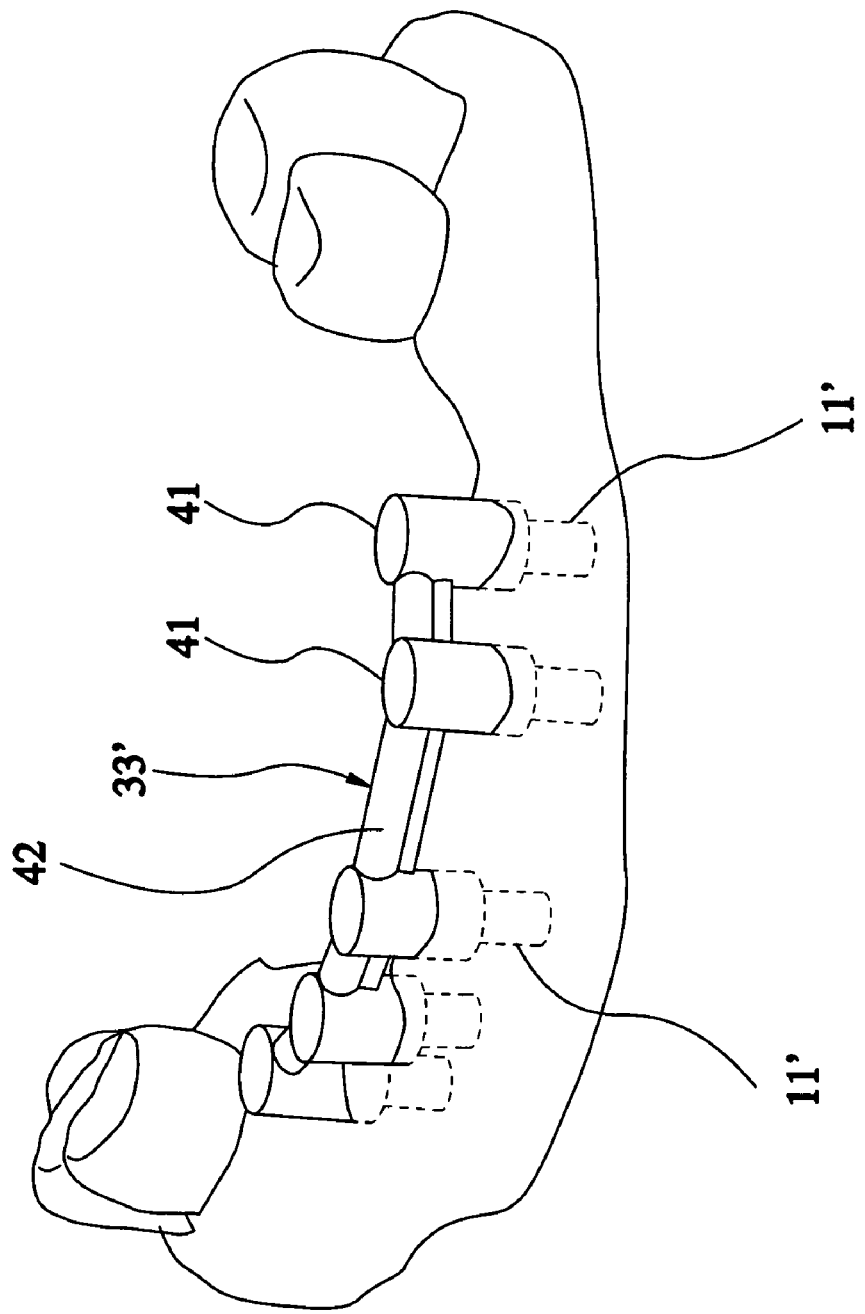
FIG. 16 is a schematic view of a second preferred embodiment of the present invention, showing that the digital dental-implant prosthesis is a digital precise dental bar.
Figure 17:
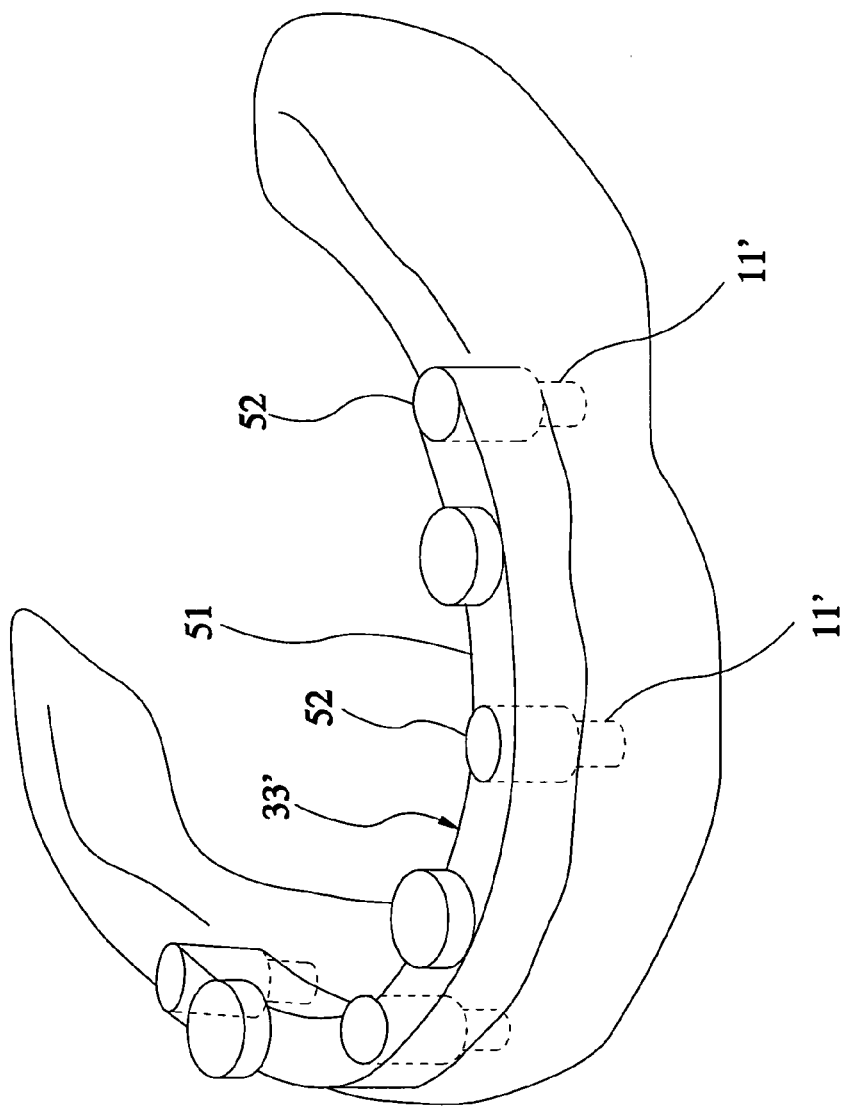
FIG. 17 is similar to FIG. 16, showing another pattern of the digital precise dental bar.
Figure 18:
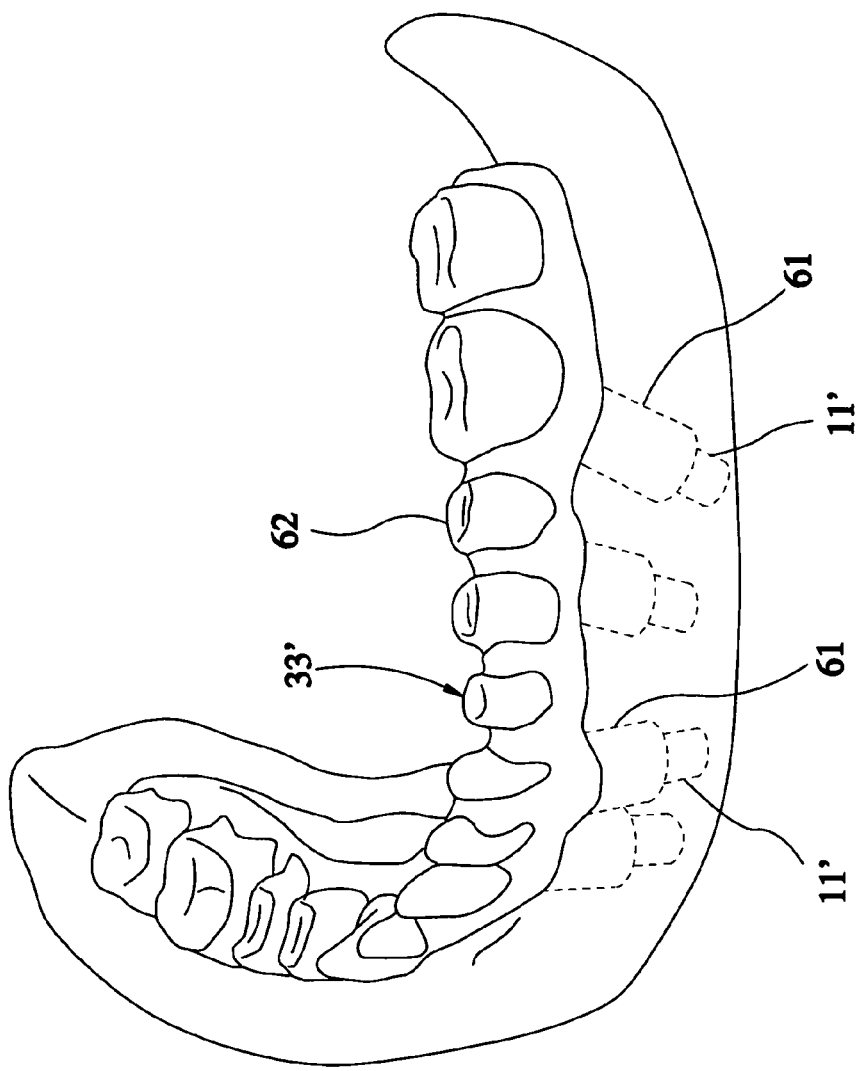
FIG. 18 is similar to FIG. 16, showing another pattern the digital precise dental bar.

Referring to FIGS. 16-18, a method of designing a dental-implant prosthesis in accordance with a second preferred embodiment of the present invention is similar to that of the first embodiment, having the following difference.

In the step a), there are multiple fixtures (not shown) in the patient's oral cavity.

In the step c), a digital dental-implant prosthesis 33' selected from a prosthetic database (not shown) in a computer (not shown) is a digital dental precision bar in this embodiment. The digital dental precision bar is combined into a digital fixture 11'. Besides, the digital dental precision bar can be used for arrangement of multiple teeth, or a denture can be fixed to the digital dental precision bar. When the actual production is intended, the digital dental precision bar includes alternative patterns recited below.

Referring to FIG. 16, the digital dental-implant prosthesis 33' (the digital dental precision bar) includes a plurality of digital coupling members 41 and a digital coupling bar 42 connected with the digital coupling members 41. The digital coupling member 41 is combined into the digital fixture 11'.

Referring FIG. 17, the digital dental-implant prosthesis 33' (the digital dental precision bar) includes a digital coupling bar 51 having a plurality of digital coupling portions 52 combined into the inferred fixtures 11'.

Referring to FIG. 18, the digital dental-implant prosthesis 33' (the digital dental precision bar) includes a plurality of digital coupling members 61 and a digital coupling bar 62 prepared on the digital coupling members 61. The digital coupling bar 62 is similar to an artificial tooth in pattern and can be directly built up with porcelain thereon to become a complete digital dental-implant prosthesis. The digital coupling members 61 are combined into the digital fixtures 11'.

What FIGS. 16-18 show is digital not solid. The other operational steps and manners are identical to those of the first embodiment, such that no more recitation is necessary.

In conclusion, the present invention includes the following advantages.

1. The present invention enables that the user does not need to acquire a solid bite mold beforehand from the patient's oral cavity, such that a lot of product time and cost can be saved and a possible distortion resulting from the acquisition of the bite mold can be avoided. Besides, the dental-implant prosthesis of the present invention can be relatively more precise.

2. The present invention enables that the connection interface of the fixture becomes relatively more obvious and the combination of the digital dental-implant prosthesis and the fixture is relatively more accurate to further adjust the most proper pattern of the digital dental-implant prosthesis, thus acquiring definite information regarding the dental occlusion and enhancing the functionality of occlusion of the artificial tooth installed later.

Although the present invention has been described with respect to a specific preferred embodiment thereof, it is in no way limited to the specifics of the illustrated structures but changes and modifications may be made within the scope of the appended claims.

What is claimed is:

1. A method of designing a dental-implant prosthesis, comprising steps of:
   a) arranging a referential jig corresponding to at least one fixture installed in a patient's oral cavity and then combining the referential jig into the at least one fixture, the referential jig having at least one feature point exposed outside the at least one fixture and dental gum in the patient's oral cavity, the fixture having a connection interface formed at a top side thereof, the referential jig having an opposite-joint interface formed at a bottom side thereof and corresponding to the connection interface;
   b) scanning the patient's oral cavity by a scanner to acquire an oral digital data, a referential-jig digital data, and a feature-point digital data, and then saving those digital data into a computer;
   c) selecting one of digital dental-implant prostheses from a prosthetic database in the computer, the selected digital dental-implant prosthesis overlapping a digital positioning jig, the digital positioning jig having the same pattern feature points as those of the referential jig, the digital positioning jig being combinable with the connection interface, the digital dental-implant prosthesis having the same opposite-joint interface formed at a bottom side thereof as that of the referential jig; operating the computer to proceed with overlapping and localization by means of the feature points of the digital positioning jig and the feature-point data of the referential-jig digital data, removing the referential-jig digital data and the digital positioning jig, and then inferring a digital fixture, a digital connection interface, and respective positions of the digital fixture and the digital connection interface to acquire a configuration data of combination and localization of the digital dental-implant prosthesis and the connection interface; and
   d) identifying the relationship among the digital dental-implant prosthesis, abutting teeth and an opposite tooth according to a space relationship between the oral digital data and the digital dental-implant prosthesis, and finally adjusting the position, size, and angle of the digital dental-implant prosthesis to acquire the digital dental-implant prosthesis 33 which is the most applicable to the patient.

2. The method as defined in claim 1, wherein each of the feature points in the step a) is convex or concave or both.

3. The method as defined in claim 1, wherein the step b) further comprises sub-steps of removing the referential jig from the at least one fixture after the patient's oral cavity is scanned and then scanning the patient's oral cavity again by the scanner to acquire a second oral digital data containing digital data of the dental gum around the at least one fixture; the step d) further comprises a sub-step of identifying a space relationship between the digital dental-implant prosthesis and the dental gum around the at least one fixture according to the second oral digital data for further adjustment and design.

4. The method as defined in claim 1, wherein the configuration digital data comprises the digital dental-implant prosthesis and an angle of and an axial direction of the digital fixture.

5. The method as defined in claim 1, wherein the digital dental-implant prosthesis is a digital abutment.

6. The method as defined in claim 1, wherein a plurality of fixtures are installed in the patient's cavity in the step a); the digital dental-implant prosthesis in the step c) is a digital precise dental bar combined into the digital fixture.

7. The method as defined in claim 6, wherein the digital process dental bar comprises a plurality of digital coupling members and a digital coupling bar connected with the digital coupling members, the digital coupling members being combined into the digital fixture.

8. The method as defined in claim 6, wherein the digital precise dental bar comprises a digital coupling bar having a plurality of coupling portions combined into the digital fixture.

9. The method as defined in claim 6, wherein the digital precise dental bar comprises a plurality of digital coupling members and a digital coupling bar prepared on the digital coupling members and being similar to an artificial tooth in pattern, whereby the digital dental-implant prosthesis can become complete by directly building up porcelain on the digital coupling bar, the digital coupling members being combined into the digital fixture.

10. The method as defined in claim 1, wherein the digital dental-implant prosthesis in the step d) comprises at least one zoom-adjustment point, at least one angle-adjustment point, and at least one position-adjustment point, whereby a user can operate the mouse cursor of the computer to click on and drag the at least one zoom-adjustment point to adjust the size of the digital dental-implant prosthesis, or to click on and drag at least one angle-adjustment point to adjust the angle of the digital dental-implant prosthesis, or to click on and drag at least one position-adjustment point to adjust a space relationship between the digital dental-implant prosthesis and the dental gum.

\* \* \* \* \*